(12) United States Patent
Costa et al.

(10) Patent No.: US 8,637,245 B2
(45) Date of Patent: Jan. 28, 2014

(54) METHOD FOR THE DETECTION OF EGFR MUTATIONS IN BLOOD SAMPLES

(75) Inventors: Rafael Rosell Costa, Badalona (ES); Miguel Taron Roca, Badalona (ES)

(73) Assignee: Pangea Biotech, S.A., Barcelona (ES)

( * ) Notice: Subject to any disclaimer, the term of this patent is extended or adjusted under 35 U.S.C. 154(b) by 516 days.

(21) Appl. No.: 12/374,307

(22) PCT Filed: Jul. 20, 2007

(86) PCT No.: PCT/EP2007/057510
§ 371 (c)(1),
(2), (4) Date: Apr. 20, 2009

(87) PCT Pub. No.: WO2008/009740
PCT Pub. Date: Jan. 24, 2008

(65) Prior Publication Data
US 2010/0009360 A1    Jan. 14, 2010

(30) Foreign Application Priority Data

Jul. 20, 2006 (EP) ..................................... 06117551

(51) Int. Cl.
*C12Q 1/68* (2006.01)
*C12P 19/34* (2006.01)
*C07H 21/04* (2006.01)

(52) U.S. Cl.
USPC ..... 435/6.11; 435/6.12; 536/23.5; 536/24.31; 536/24.33

(58) Field of Classification Search
None
See application file for complete search history.

(56) References Cited

U.S. PATENT DOCUMENTS

2005/0272083 A1* 12/2005 Seshagiri ........................ 435/6

OTHER PUBLICATIONS

Pan, Q. et al. Journal of Molecular Diagnostics 7(3):396-403 (Aug. 2005).*
Bell, D. et al., "A blood based test for epidermal growth factor receptor mutations in Lung Cancer", "Clin. Cancer Res.", Jul. 1, 2006, pp. 3875-3877, vol. 12, No. 13.
Belokhvostov, A. et al. , "Detection of tumor-derived DNA with EGFR mutations in different biological samples from cancer patients: feasibility and optimization of the method, (Abstract Only)", Sep. 12, 2006, pp. 1-2, Publisher: First AACR International Conference on Molecular Diagnositics in Cancer Therapeutic Development.
Gou, J. et al., "Effect of EGFR mutations on gefitinib in advanced previous treated non-small cell lung cancer (Abstract Only)", "Journal of Clinical Oncology", May 20, 2008, vol. 26, No. 15S.
Holland, W. et al., "Enhanced detection of EGFR mutations in plasma from non-small cell lung cancer (NSCLC) patients using Scorpion primers", "Journal of Clinical Oncology", Jun. 20, 2007, pp. 1-2, vol. 25, No. 18S.
Kimura, H. et al., "Detection of Epidermal Growth Factor Receptor Mutations in Serum as a Predictor of the Response to Gefitinib in Patients", "Clin. Cancer Research", Jul. 1, 2006, pp. 3915-3921, vol. 12, No. 13.
Kimura, H. et al., "Evaluation of epidermal growth factor receptor mutation status in serum DNA as a predictor or response to gefitinib", "British Journal of Cancer", , pp. 778-784, vol. 97, Sep. 2007.
Kimura, H. et al., "EGFR Mutation of Tumor and Serum in Gefitnib-Treated Patients with Chemotherapy-Naive Non Small Cell Lung Cancer", "Journal of Thoracic Oncology", Mar. 2006, pp. 260-267, vol. 1, No. 3.
Maheswaran, S. et al., "Detection of Mutations in EGFR in Circulating Lung Cancer Cells", "New England Journal of Medicine", Jul. 2, 2008, pp. 1-12, vol. 359.
Nagai, Y. et al., "Genetic Heterogeneity of the Epidermal Growth Factor Receptor in Non Small Cell Lung Cancer Cell Lines Revealed by a Rapid and Sensitive Detection System, the Peptide Nucleic Acid-Locked Nucleic Acid PCR Clamp", "Cancer Research", Aug. 15, 2005, pp. 7276-7282, vol. 65, No. 16.
Ray, A. et al., "Peptide nucleic acid (PNA): its medical and biotechnical applications and promise for the future", "The FASEB Journal", 2000, pp. 1041-1060, vol. 14.
Sanders, H. et al., "A sensitive method for detection of EGFR gene mutations in plasma (Abstract Only)", "Journal of Clinical Oncology", Jun. 20, 2007, vol. 25, No. 18S.
Urata, M. et al., "High Sensitivity Detection of the A3243G Mutation of Mitochondrial DNA by a combination of Allele-specific PCR and peptide specific nucleic acid clamping", "Clinical Chemistry", 2004, pp. 2045-2051, vol. 2550, No. 11.
Jimeno, J. , "Declaration of J. Jimeno to EPO in corresponding EP Application No. 07787764.5", "Declaration of J. Jimeno", Oct. 16, 2009, pp. 1-2.
Pao, W. et al., "Acquired resistance of lung adenocarcinomas to Gefitinib or Erlotinib is associated with a second mutation in the EGFR..", "PLoS Medicine", Mar. 2005, pp. 225-235, vol. 2, No. 3.
Taron, M. et al. , "Final Study Report DxS EGFR Mut-kit comparison", Jun. 15, 2009, pp. 1-16, Publisher: Pangea Biotech Corporation.

* cited by examiner

*Primary Examiner* — Diana Johannsen
(74) *Attorney, Agent, or Firm* — Hultquist IP PLLC; Steven J. Hultquist; Mary B. Grant

(57) ABSTRACT

The present invention refers to the detection of EGFR mutations in a blood (serum/plasma) sample from a subject. The method comprises: (i) obtaining the DNA from said sample; (ii) amplifying the nucleic acid sequence corresponding to a specific region of the EGFR gene by means of PCR using a Protein-Nucleic Acid probe; 10 and (iii) detecting said mutation.

6 Claims, No Drawings

METHOD FOR THE DETECTION OF EGFR MUTATIONS IN BLOOD SAMPLES

CROSS-REFERENCE TO RELATED APPLICATIONS

This application is a U.S. national phase under the provisions of 35 USC §371 of International Application No. PCT/EP07/57510 filed Jul. 20, 2007, which in turn claims priority of European Patent Application No. 06117551.9 filed Jul. 20, 2006. The disclosures of such international application and European priority application are hereby incorporated herein by reference in their respective entireties, for all purposes.

FIELD OF THE INVENTION

The present invention refers to the detection of EGFR mutations in a blood (serum/plasma) sample from a subject.

BACKGROUND

Lung cancer is the leading cause of cancer-related mortality in both men and women. The prevalence of lung cancer is second only to that of prostate cancer in men and breast cancer in women. Lung cancer recently surpassed heart disease as the leading cause of smoking-related mortality. In addition, most patients who develop lung cancer smoke and have smoking-related damage to the heart and lungs, making aggressive surgical or multimodality therapies less viable options. Most lung carcinomas are diagnosed at an advanced stage, conferring a poor prognosis.

Non-small cell lung cancer (NSCLC) accounts for approximately 75% of all lung cancers. NSCLC is a heterogeneous aggregate of histologies. The most common histologies are epidermoid or squamous carcinoma, adenocarcinoma, and large cell carcinoma.

Several studies have attempted to identify clinical, laboratory, and molecular markers that may help clinicians and researchers distinguish subgroups of NSCLC patients. Along these lines, various studies have shown that epidermal growth factor receptor (EGFR) is over-expressed in 40 to 80 percent of non-small cell lung cancers and many other epithelial cancers.

Aberrant epidermal growth factor receptor (EGFR) signalling is critical for limiting sensitivity to anticancer agents and ligand-independent tyrosine kinase activation of EGFR is often caused by EGFR mutations in the extracellular domain, which has been observed in various tumour types, such as glioblastoma multiforme. EGFR signalling is triggered by the binding of growth factors, such as epidermal growth factor (EGF). Autophosphorylation and transphosphorylation of the receptors through their tyrosine kinase domains leads to the recruitment of downstream effectors and the activation of proliferative and cell-survival signals.

Two mutations account for approximately 90% of EGFR mutations reported to date in lung adenocarcinomas. In Caucasian population, the most common mutation type, seen in around 65% of cases with EGFR mutations, is a short in-frame deletion of 9, 12, 15, 18, or 24 nucleotides in exon 19. The second most common mutation, seen in about 35% of cases with EGFR mutations, is a point mutation (CTG to CGG) in exon 21 at nucleotide 2573, that results in substitution of leucine by arginine at codon 858 (L858R) adjacent to the DFG motif in the carboxy-terminal lobe in the activation loop of the kinase.

These EGFR mutations are bona fide somatic mutations in NSCLC and have not been identified in other primary tumour types. Further, EGFR mutations are a strong determinant of tumor response to gefitinib in non-small cell lung cancer (NSCLC). Other much less common mutations have been described in exons 18, 20, and 21.

So far, screening for these mutations has been based on direct sequencing or single-strand conformation polymorphism analysis. Nucleic acid amplification methods (for example, the polymerase chain reaction) allow the detection of small numbers of mutant molecules among a background of normal ones. While alternative means of detecting small numbers of tumor cells (such as flow cytometry) have generally been limited to hematological malignancies, nucleic acid amplification assays have proven both sensitive and specific in identifying malignant cells and for predicting prognosis following chemotherapy.

Various nucleic acid amplification strategies for detecting small numbers of mutant molecules in solid tumor tissue have been developed. For example, one sensitive and specific method identifies mutant ras oncogene DNA on the basis of failure to cleave a restriction site at the crucial 12th codon (Kahn et al. Rapid and sensitive nonradioactive detection of mutant K-ras genes via 'enriched' PCR amplification. Oncogene. 1991 June; 6(6):1079-83). Similar protocols can be applied to detect any mutated region of DNA in a neoplasm, allowing detection of other oncogene DNA or tumor-associated DNA. Since mutated DNA can be detected not only in the primary cancer but in both precursor lesions and metastatic sites, nucleic acid amplification assays provide a means of detecting and monitoring cancer both early and late in the course of disease.

Other studies have used nucleic acid amplification assays to analyze the peripheral blood of patients with cancer in order to detect intracellular DNA extracted from circulating cancer cells in patients. However, it must be emphasized that these studies attempt to use nucleic acid-based amplification assays to detect extracted intracellular DNA within circulating cancer cells. The assay is performed on the cellular fraction of the blood from patients having cancer using the cell pellet or cells within whole blood, and the serum or plasma fraction is conventionally ignored or discarded prior to analysis. Since such an approach requires the presence of metastatic circulating cancer cells (for non-hematologic tumors), it is of limited clinical use in patients with early cancers, and it is not useful in the detection of non-hematologic non-invasive neoplasms or pre-malignant states.

It is known in the prior art that small but significant amounts of normal DNA circulate in the blood of healthy people and this amount has been found to increase in cancer states. The prior art contains disclosure that mutant oncogene DNA could be detected in peripheral blood plasma or serum of cancer patients. However, these reports have also been generally limited to patients with advanced cancer or known neoplastic or proliferative disease. Some authors (Kimura et al., 2006. EGFR Mutation of Tumor and Serum in Gefitinib-Treated Patients with Chemotherapy-Naive Non-small Cell Lung Cancer) have described that mutations at EGFR gene can be detected in serum samples from patients suffering from NSCLC. Said document describes detection of such mutations by means of PCR and sequencing using primers flanking said mutations.

SUMMARY OF THE INVENTION

The present invention refers to a method for the detection of mutations at the EGFR gene in a blood sample from a subject said method comprising:

(i) obtaining the DNA from said sample;
(ii) amplifying the nucleic acid sequence corresponding to a specific region of the EGFR gene by means of PCR using a Protein-Nucleic Acid probe; and
(iii) detecting said mutation.

Here, the inventors have developed and validated a polymerase chain reaction (PCR)-based assay for the detection of the most common EGFR mutations in plasma/serum samples. This assay offers higher analytical sensitivity by enhancing amplification of mutant alleles in the samples to be analysed by means of using a Protein-Nucleic Acid (PNA) probe compared to standard methods, in which primers flanking the mutations are employed for PCR amplification and further sequencing analysis. Thus, a robust and accessible approach is here provided to the rapid identification of most lung cancer patients who are likely to respond to specific EGFR inhibitors.

Additionally, while direct analysis of neoplastic tissue is frequently difficult or impossible (such as in instances of occult, unrecognized disease), the method described above has the advantage of using blood, such as peripheral blood, for the detection of said mutation. Peripheral blood is easily accessible and amenable to nucleic acid-based assays.

DETAILED DESCRIPTION OF THE INVENTION

In order to facilitate the understanding of the present description, the meaning of some terms and expressions in the context of the invention will be explained below:

The term "subject", refers to a male or female human of any age or race. Preferably it includes humans having or suspected of having non-small cell lung cancer (NSCLC). Diagnostic methods for NSCLC and the clinical delineation of NSCLC diagnoses are well known to those of ordinary skill in the medical arts. As examples, methods for identifying subjects suspected of having NSCLC may include physical examination, subject's family medical history, subject's medical history, lung biopsy, or a number of imaging technologies such as ultrasonography.

The term "nucleic acid" refers to a multimeric compound comprising nucleosides or nucleoside analogues which have nitrogenous heterocyclic bases, or base analogues, which are linked by phosphodiester bonds to form a polynucleotide.

The term "DNA" refers to deoxyribonucleic acid. A DNA sequence is a deoxyribonucleic sequence. DNA is a long polymer of nucleotides and encodes the sequence of the amino acid residues in proteins using the genetic code.

The term "Protein-Nucleic Acid probe" refers to a synthetic DNA analog in which the phosphodiester backbone is replaced by repetitive units of N-(2-aminoethyl) glycine to which the purine and pyrimidine bases are attached via a methyl carbonyl linker.

In one aspect, the invention refers to a method, herein referred to as "method of the invention", for the detection of mutations at the EGFR gene in a blood sample from a subject said method comprising:
(i) obtaining the DNA from said sample;
(ii) amplifying the nucleic acid sequence corresponding to a specific region of the EGFR gene by means of PCR using a Protein-Nucleic Acid probe; and
(iii) detecting said mutation.

The method of the invention can be used to detect any mutation at the EGFR gene. In a particular embodiment of the invention, the mutation at the EGFR gene to be detected is selected from the group consisting of: ELREA deletions at the exon 19, the L858R mutation at the exon 21 and the T790M mutation at exon 21.

Samples

Illustrative, non limitative, examples of samples from which nucleic acids can be extracted and analysed using the method of the invention include, but are not limited to, both normal and cancerous blood (serum or plasma) and other body fluids containing nucleic acids that can be detected.

In order to carry out the method of the invention, a sample is obtained from the subject under study. In a particular embodiment, the sample is a blood sample. Samples can be obtained from subjects previously diagnosed or not with NSCLC, or from subjects who are receiving or have previously received anti-NSCLC treatment. In an embodiment, the sample is a sample from a subject having normal lung function tissue, i.e., a subject with no evidence of NSCLC.

In the practice of the invention blood is drawn by standard methods into a collection tube, preferably comprising siliconized glass, either without anticoagulant for preparation of serum or with EDTA, heparin, or similar anticoagulants, most preferably EDTA, for preparation of plasma. Plasma may optionally be subsequently converted to serum by incubation of the anticoagulated plasma with an equal volume of calcium chloride at 37° C. for a brief period, most preferably for 1-3 minutes, until clotting takes place. The clot may then be pelleted by a brief centrifugation and the deproteinized plasma removed to another tube. Alternatively, the centrifugation may be omitted. Serum can also be obtained using clot activator tubes.

DNA Amplification

In a particular embodiment of the invention, the serum or plasma may be utilized directly for identification of the mutant DNA. In another particular embodiment, nucleic acid is extracted from plasma or serum as an initial step of the invention. In such cases, the total DNA extracted from said samples would represent the working material suitable for subsequent amplification.

Once the sample has been obtained, amplification of nucleic acid is carried out. In a particular embodiment, the amplification of the DNA is carried out by means of PCR. The general principles and conditions for amplification and detection of nucleic acids, such as using PCR, are well known for the skilled person in the art. In particular, the Polymerase Chain Reaction (PCR) carried out by the method of the present invention uses appropriate and specific oligonucleotide primers or amplification oligonucleotides to specifically amplify the EGFR target sequences. Illustrative, non limitative, examples of such amplification oligonucleotides include the sequences of SEQ ID NO: 1 and SEQ ID NO: 2. The terms "oligonucleotide primers" or "amplification oligonucleotides" are herein used indistinguishably and refer to a polymeric nucleic acid having generally less than 1,000 residues, including those in a size range having a lower limit of about 2 to 5 residues and an upper limit of about 500 to 900 residues. In preferred embodiments, oligonucleotide primers are in a size range having a lower limit of about 5 to about 15 residues and an upper limit of about 100 to 200 residues. More preferably, oligonucleotide primers of the present invention are in a size range having a lower limit of about 10 to about 15 residues and an upper limit of about 17 to 100 residues. Although oligonucleotide primers may be purified from naturally occurring nucleic acids, they are generally synthesized using any of a variety of well known enzymatic or chemical methods. In a particular embodiment of the invention, such oligonucleotide primers enable the specific amplification of the DNA fragments corresponding to the deletion of specific nucleotides in the exon 19 at the EGFR gene.

Thus, in a particular embodiment, the method of the invention can be used for the detection of ELREA deletions at the exon 19. In a preferred embodiment, the present invention refers to a method for the detection of 9, 12, 15, 18, or 24 nucleotides deletions in the exon 19 at the EGFR gene. In another particular embodiment, the method of the invention can be used for the detection of the L858R mutation at the exon 21 of the EGFR gene. In another embodiment, the method of the invention can be used for the detection of the T790M mutations in exon 21 of the EGFR gene.

The term "amplification oligonucleotide" refers to an oligonucleotide that hybridizes to a target nucleic acid, or its complement, and participates in a nucleic acid amplification reaction. Amplification oligonucleotides include primers and promoter-primers in which the 3' end of the oligonucleotide is extended enzymatically using another nucleic acid strand as the template. In some embodiments, an amplification oligonucleotide contains at least about 10 contiguous bases, and more preferably about 12 contiguous bases, that are complementary to a region of the target sequence (or its complementary strand). Target-binding bases are preferably at least about 80%, and more preferably about 90% to 100% complementary to the sequence to which it binds. An amplification oligonucleotide is preferably about 10 to about 60 bases long and may include modified nucleotides or base analogues.

The terms "amplify" or "amplification" refer to a procedure to produce multiple copies of a target nucleic acid sequence or its complement or fragments thereof (i.e., the amplified product may contain less than the complete target sequence). For example, fragments may be produced by amplifying a portion of the target nucleic acid by using an amplification oligonucleotide which hybridizes to, and initiates polymerization from, an internal position of the target nucleic acid. Known amplification methods include, for example, polymerase chain reaction (PCR) amplification, replicase-mediated amplification, ligase chain reaction (LCR) amplification, strand-displacement amplification (SDA) and transcription-associated or transcription-mediated amplification (TMA). PCR amplification uses DNA polymerase, primers for opposite strands and thermal cycling to synthesize multiple copies of DNA or cDNA. Replicase-mediated amplification uses QB-replicase to amplify RNA sequences. LCR amplification uses at least four different oligonucleotides to amplify complementary strands of a target by using cycles of hybridization, ligation, and denaturation. SDA uses a primer that contains a recognition site for a restriction endonuclease and an endonuclease that nicks one strand of a hemimodified DNA duplex that includes the target sequence, followed by a series of primer extension and strand displacement steps. An isothermal strand-displacement amplification method that does not rely on endonuclease nicking is also known. Transcription-associated or transcription-mediated amplification uses a primer that includes a promoter sequence and an RNA polymerase specific for the promoter to produce multiple transcripts from a target sequence, thus amplifying the target sequence.

Preferred embodiments of the present invention amplify the EGFR target sequences using the present amplification oligonucleotides in a polymerase chain reaction (PCR) amplification. One skilled in the art will appreciate that these amplification oligonucleotides can readily be used in other methods of nucleic acid amplification that uses polymerase-mediated primer extension.

In the amplifying step of the method of the invention, the nucleic acid sequence corresponding to a specific region of the EGFR gene is amplified by means of PCR using a Protein-Nucleic Acid (PNA) probe. PNA probes are nucleic acid analogs in which the sugar phosphate backbone of a natural nucleic acid has been replaced by a synthetic peptide backbone, usually formed from N-(2-aminoethyl)-glycine units, resulting in an achiral and uncharged mimic. This new molecule is chemically stable and resistant to hydrolytic (enzymatic) cleavage and thus not expected to be degraded inside a living cell. Despite all these variations from natural nucleic acids, PNA is still capable of sequence-specific binding to DNA as well as RNA obeying the Watson-Crick hydrogen bonding rules. Its hybrid complexes exhibit extraordinary thermal stability and display unique ionic strength properties. In many applications, PNA probes are preferred to nucleic acid probes because, unlike nucleic acid/nucleic acid duplexes which are destabilized under conditions of low salt, PNA/nucleic acid duplexes are formed and remain stable under conditions of very low salt. Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target sequence combination is often found by the well known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

PNA oligomers can be prepared following standard solid-phase synthesis protocols for peptides (Merrifield, B. 1986. Solid-phase synthesis. Science 232, 341-347) using, for example, a (methyl-benzhydryl)amine polystyrene resin as the solid support. PNAs may contain a chimeric architecture, such as a PNA/DNA chimera, where a PNA oligomer is fused to a DNA oligomer.

Clinical samples contain DNA molecules with the wild-type allele in addition to DNA molecules with the mutant allele. So, under normal conditions, it is difficult to detect EGFR mutations (mutant allele) in a large background of wild-type EGFR genes (wild-type allele). In a particular case, the PNA probe utilized by the inventors is capable of specifically recognize and hybridize with the wild-type EGFR sequence. As an illustrative, non limitative example, the PNA probe to be used for carrying out the method of the present invention comprises the PNA probe described as the SEQ ID NO:3 in the Example accompanying the present invention. Such probe is added to the PCR reaction mix thus inhibiting amplification of the wild-type allele and favouring amplification of the mutant allele present in the sample, i.e. EGFR mutant, facilitating its posterior detection. Those of ordinary skill in the art will appreciate that a suitable PNA probe do not need to have exactly these probing nucleic acid sequences to be operative but often modified according to the particular assay conditions. For example, shorter PNA probes can be prepared by truncation of the nucleic acid sequence if the stability of the hybrid needs to be modified to thereby lower the Tm and/or adjust for stringency. Similarly, the nucleic acid sequence may be truncated at one end and extended at the other end as long as the discriminating nucleic acid sequence remains within the sequence of the PNA probe. Such variations of the probing nucleic acid sequences within the parameters described herein are considered to be embodiments of this invention.

As it can be observed in the Example 1 of the present invention, the conditions of the polymerase chain reaction using such PNA probe applied in the method of the present invention are such that only 40 cycles of amplification are sufficient for the obtainment of a precise PCR amplification product comprising a 120 bp genomic fragment including the mutation of interest of exon 19 at the EGFR gene.

The general conditions for the PCR of the method of the present invention are as illustrated in the Example 1 of the present invention. In this example, the DNA used for the PCR amplification reaction is from plasma/serum samples.

Detection of DNA Mutation

Many methods for detecting and analysing the PCR amplification products have been previously disclosed. Particularly, detection of DNA sequence mutants may proceed by any of a number of methods known to those skilled in the art (Kilger et al., 1997, Nucleic Acids Res. 25: 2032-4). In a particular embodiment of the invention, the detecting step of the method of the invention is carried out by means of nucleic acid sequencing. Illustrative, non limitative, examples of nucleic acid sequencing methods are cycle sequencing (Sarkar et al., 1995, Nucleic Acids Res. 23: 1269-70) or direct dideoxynucleotide sequencing, in which some or the entire DNA of interest that has been harvested from the sample is used as a template for sequencing reactions. An oligonucleotide primer or set of primers specific to the gene or DNA of interest is used in standard sequencing reactions. Other methods of DNA sequencing, such as sequencing by hybridization, sequencing using a "chip" containing many oligonucleotides for hybridization (as, for example, those produced by Affymetrix Corp.; Ramsay et al., 1998, Nature Biotechnology 16: 40-44; Marshall et al., 1998, Nature Biotechnology 16: 27-31), sequencing by HPLC (DeDionisio et al., 1996, J Chromatogr A 735: 191-208), and modifications of DNA sequencing strategies such as multiplex allele-specific diagnostic assay (MASDA; Shuber et al., 1997, Hum. Molec. Genet. 6: 337-47), dideoxy fingerprinting (Sarkar et al., 1992, Genomics 13: 441-3; Martincic et al., 1996, Oncogene 13: 2039-44), and fluorogenic probe-based PCR methods (such as Taqman; Perkin-Elmer Corp.; Heid et al., 1996, Genome Res. 6: 986-94) and cleavase-based methods may be used.

Alternatively, amplification can be carried out using primers that are appropriately labelled, and the amplified primer extension products can be detected using procedures and equipment for detection of the label. Preferably probes of this invention are labeled with at least one detectable moiety, wherein the detectable moiety or moieties are selected from the group consisting of: a conjugate, a branched detection system, a chromophore, a fluorophore, a spin label, a radio-isotope, an enzyme, a hapten, an acridinium ester and a luminescent compound. As an illustrative, non limitative, example, in the method of the present invention the primers used can labelled with a fluorophore. More particularly, the reverse primer of the method of the present invention is labelled with the 6-FAM fluorophore at its 5' end. This fluorophore emits fluorescence with a peak wavelength of 522 nm. The PCR can be carried out using one of the primers labelled with, for example, either FAM, HEX, VIC or NED dyes.

In a preferred embodiment of the invention, the posterior detection and analysis of the DNA amplified with the method of the invention is carried out by the GeneScan technique as it is illustrated in the Example accompanying the present invention. Thus, as an illustrative, non limitative, example for carrying out the detecting step of the method of the invention, an aliquot of the PCR reaction (typically 1 µl) is added to 9 µl of formamide HI-DI and 0.25 µl of GeneScan marker—500 LIZ size standard. After denaturation, the sample is placed in the ABI 3130 Genetic Analyzer and capillary electrophoresis is carried out. The raw data is analysed using GeneScan software. This analysis is very important since the PCR products will be sized by extrapolation to an in-sample size standard. Using this technique inventors are able to detect in a very precise and accurate manner the mutation of interest.

The invention is further illustrated with the following Examples, which is provided to illustrate certain embodiments of the present invention and is not to be construed as limiting the invention.

EXAMPLE 1

Determination of the ELREA Deletion at the Exon 19 of the EGFR Gene by GeneScan

Materials and Methods:

1—Sample Collection

Venous blood (10 ml) from each subject was placed into tubes containing 50 mmol of EDTA (ethylenediaminetetraacetic acid) per liter, and genomic DNA was isolated with the QIAmp® DNA blood Mini kit (Qiagen, Germany), according to manufacturer's instructions.

2—Genescan Reaction Preparation 1.1—Materials

Abi Prism 3130 DNA Analyser (Perkin-Elmer, Applied Biosystems)

96 Well optical Reaction plate (Applied Biosystems, Cat. No, 4306737)

1.2—PCR Reaction mix with PNA probe

The PCR reaction mix was made as follows:

2.5 µl Buffer 10× (Ecogen)
0.5 µl 50 mM $MgCl_2$ (Ecogen)
0.625 µl 10 mM dNTPs (Promega)
1.25 µl 10 µM of each primer
0.1 µl TAQ polymerase (Ecogen)
12.5 µl 5 mM PNA probe (Applied Biosystems)
5 µl DNA from serum or plasma
Add sterile distilled $H_2O$ to a final volume of 25 µl.

1.3—PCR Reaction Mix without PNA Probe

The PCR reaction mix was made as follows:

2.5 µl Buffer 10× (Ecogen)
0.5 µl 50 mM $MgCl_2$ (Ecogen)
0.625 µl 10 mM dNTPs (Promega)
1.25 µl 10 µM of each primer
0.1 µl TAQ polymerase (Ecogen)
5 µl DNA from serum or plasma
Add sterile distilled $H_2O$ to a final volume of 25 µl.

The reverse primer was labelled with the 6-FAM fluorophore (6-FAM emits fluorescence with a peak wavelength of 522 nm).

```
                                           (SEQ ID NO: 1)
Primer Forward:     ACTCTGGATCCCAGAAGGTGAG (SEQ ID NO: 2)
Primer Reverse:     6-FAM-CCACACAGCAAAGCAGAAACTC (SEQ ID NO: 3)
PNA probe sequence: Ac-AGATGTTGCTTCTCTTA
```

1.3—PCR Program

The PCR was performed as follows: 95° C. during 5 minutes followed by 40 cycles at 95° C. for 30 seconds, 58° C. for 30 seconds and 72° C. for 1 minute, and a final extension of 72° C. for 5 minutes.

3—GeneScan Preparation

9 µl formamide HI-DI (Applied Biosystems)

0.25 µl GeneScan marker—500 LIZ size standard (Applied Biosystems)

1 µl final PCR product diluted

Samples were denatured at 93° C. for 3 minutes and cooled on ice for 10 minutes. They were then subjected to capillary electrophoresis and subsequent subjected to an excitation wavelength of 494 nm for detection of emission wavelength at 522 nm on the ABI 3130 DNA analyzer.

Results:

A total of 41 serum/plasma samples were analysed by GeneScan for detection of deletions in exon 19. All samples analysed were from patients with positive mutations in tumor tissue.

GeneScan analysis results show that 55% of the samples with positive mutations in tumor tissue were also positive by Genescan analysis (Table 1).

TABLE 1

Exon 19 EGFR mutation analysis in serum/plasma of patients with positive mutations in tumor tissue.

| EGFR mutations in tumor | S/P positive | S/P negative |
|---|---|---|
| N = 41 | N = 22 (55%) | N = 19 (45%) |
| Male | 8 | 8 |
| Female | 14 | 11 |
| Erlotinib | | |
| 1st-line | 12 | 11 |
| 2nd-line | 10 | 8 |
| Never smoker | 15 | 12 |
| Ex-smoker | 7 | 6 |
| Smoker | 0 | 1 |
| Blood extraction | | |
| Before treatment | 16 | 9 |
| After treatment | 5 | 8 |
| Unknown | 1 | 2 |
| CR + PR | 1 + 12 | 1 + 6 |
| SD + PD | 0 + 1 | 2 + 0 |

EXAMPLE 2

Determination of the L858R mutation in exon 21 of the EGFR gene by Genescan

Materials and Methods:
1—Sample Collection
Venous blood (10 ml) from each subject was placed into tubes containing 50 mmol of EDTA (ethylenediaminetetraacetic acid) per liter, and genomic DNA was isolated with the QIAmp® DNA blood Mini kit (Qiagen, Germany), according to manufacturer's instructions.
2—Taqman Reaction (5'Nuclease Activity Assay)
1.1—Materials
AB 7000 or 7900HT (Applied Biosystems)
1.2—PCR Reaction (5'Nuclease Activity Assay) Mix with PNA Probe The PCR reaction mix was made as follows (Table 2):

TABLE 2

| Reaction Mix | Final Concentr | Stock Concentr | For each sample (µl) |
|---|---|---|---|
| Universal TaqMan Master Mix | 1x | 2x | 12.5 |
| Primer F | 0.6 µM | 10 µM | 1.5 |
| Primer R | 0.6 µM | 10 µM | 1.5 |
| Probe wt-VIC | 0.2 µM | 10 µM | 0.5 |
| Probe mut-FAM | 0.2 µM | 10 µM | 0.5 |

TABLE 2-continued

| Reaction Mix | Final Concentr | Stock Concentr | For each sample (µl) |
|---|---|---|---|
| PNA | 0.5 µM | 10 µM | 1.25 |
| Serum or plasma DNA | | | 5 |
| Water | | | 5.25 |

The PCR was performed as follows: 60° C. durante 2 min followed by 50 cycles at 95° C. during 10 min followed by 50 cycles at 95° C. for 15 seconds and 60° C. during 1 min 30 sec.

3—Primers, Probes and PNA

The probe for detecting wild-type sequences was labeled with the fluorochrome VIC, whereas the probe for detecting the mutant allele was labeled with the fluorochrome FAM

```
Primer      AACACCGCAGCATGTCAAGA    (SEQ ID NO: 4)
Forward:

Primer      TTCTCTTCCGCACCCAGC      (SEQ ID NO: 5)
Reverse:
```

Probe for the detection of the wild-type allele labelled with the fluorochrome VIC:

```
VIC-TCACAGATTTTGGGCTGGCCAAAC-TAMRA (SEQ ID NO: 6)
```

Probe for the detection of the mutant allele labelled with the fluorochrome FAM:

```
6-FAM-CAGATTTTGGGCGGGCCAAAC-TAMRA  (SEQ ID NO: 7)

PNA Probe: AGTTTGGCCAGCCCA             (SEQ ID NO: 8)
```

Results:

A total of 41 serum/plasma samples were analysed by GeneScan for detection of mutations in L858R. All samples analysed were from patients with positive mutations in tumour tissue.

5' nuclease activity assay analysis results show that 55% (L858R) of the samples with positive mutations in tumour tissue were also positive by this analysis (Table 3).

TABLE 3

| EGFR mutations in tumor | S/P positive | S/P negative |
|---|---|---|
| N = 41 | N = 22 (55%) | N = 19 (45%) |

EXAMPLE 3

Determination of the T790M Mutations in Exon 21 of the EGFR Gene by Taqman Reaction Materials and Methods:
1—Sample Collection
Venous blood (10 ml) from each subject was placed into tubes containing 50 mmol of EDTA (ethylenediaminetetraacetic acid) per liter, and genomic DNA was isolated with the QIAmp® DNA blood Mini kit (Qiagen, Germany), according to manufacturer's instructions.
2—Taqman Reaction (5'Nuclease Activity Assay)
1.1—Materials
AB 7000 or 7900HT (Applied Biosystems)
1.2—PCR Reaction (5'Nuclease Activity Assay) Mix with PNA Probe The PCR reaction mix was made as in example 2 (see Table 2):

The PCR was performed as follows: 60° C. for 2 min followed by 50 cycles at 95° C. during 10 min followed by 50 cycles at 95° C. for 15 seconds and 60° C. during 1 min 30 sec.

3—Primers, Probes and PNA

The probe for detecting wild-type sequences was labeled with the fluorochrome VIC, whereas the probe for detecting the mutant allele was labelled with the fluorochrome FAM

```
Primer Forward:  AGGCAGCCGAAGGGC    (SEQ ID NO: 9)

Primer Reverse:  CCTCACCTCCACCGTGCA (SEQ ID NO: 10)
```

Probe for the detection of the wild-type allele labelled with the fluorochrome VIC:

```
VIC-TGAGCTGCGTGATGA-MGB       (SEQ ID NO: 11)
```

Probe for the detection of the mutant allele labelled with the fluorochromeFAM:

```
6-FAM-TGAGCTGCATGATGA-MGB     (SEQ ID NO: 12)

PNA Probe: TCATCACGCAGCTC     (SEQ ID NO: 13)
```

Results:

A total of 4 serum/plasma samples were analysed. All samples analysed were from patients with positive mutations in tumour tissue.

5'Nuclease activity assay analysis results show that 75% (T790M) of the samples with positive mutations in tumour tissue were also positive by this analysis (Table 4 for T790M).

TABLE 4

| EGFR mutations in tumor | S/P positive | S/P negative |
| --- | --- | --- |
| N = 4 | N = 3 (75%) | N = 1 (25%) |

SEQUENCE LISTING

```
<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: Forward primer designed for the detection of
      ELREA deletion at the exon 19 of the EGFR gene

<400> SEQUENCE: 1
actctggatc ccagaaggtg ag                                              22

<210> SEQ ID NO 2
<211> LENGTH: 22
<212> TYPE: DNA
<213> ORGANISM: Artificial Sequence
<220> FEATURE:
<223> OTHER INFORMATION: Reverse primer designed for the detection of
      ELREA deletion at the exon 19 of the EGFR gene. The primer is
      modified by labelling with the 6-FAM fluorophore its 5' end

<400> SEQUENCE: 2
ccacacagca aagcagaaac tc                                              22

<210> SEQ ID NO 3
<211> LENGTH: 17
<212> TYPE: DNA
<213> ORGANISM: Artificial Sequence
<220> FEATURE:
<223> OTHER INFORMATION: Protein-Nucleic Acid (PNA) probe designed for
      the detection of ELREA deletion at the exon 19 of the EGFR gene.
      The primer is modified with an Ac group at its 5' end

<400> SEQUENCE: 3
agatgttgct tctctta                                                    17

<210> SEQ ID NO 4
<211> LENGTH: 20
<212> TYPE: DNA
<213> ORGANISM: Artificial Sequence
<220> FEATURE:
<223> OTHER INFORMATION: Forward primer designed for detection of the
```

L858R mutation in exon 21 of the EGFR gene

<400> SEQUENCE: 4
aacaccgcag catgtcaaga                                               20

<210> SEQ ID NO 5
<211> LENGTH: 18
<212> TYPE: DNA
<213> ORGANISM: Artificial Sequence
<220> FEATURE:
<223> OTHER INFORMATION: Reverse primer designed for detection of the
      L858R mutation in exon 21 of the EGFR gene

<400> SEQUENCE: 5
ttctcttccg cacccagc                                                 18

<210> SEQ ID NO 6
<211> LENGTH: 24
<212> TYPE: DNA
<213> ORGANISM: Artificial Sequence
<220> FEATURE:
<223> OTHER INFORMATION: Probe designed for the detection of wild-type
      EGFR gene allele in the region of the L858R mutation. The primer
      is modified with a VIC group at the 5' end

<400> SEQUENCE: 6
tcacagattt tgggctggcc aaac                                          24

<210> SEQ ID NO 7
<211> LENGTH: 21
<212> TYPE: DNA
<213> ORGANISM: Artificial Sequence
<220> FEATURE:
<223> OTHER INFORMATION: Probe designed for the detection of L858R
      mutant in the EGFR gene allele; the primer is modified with a
      6-FAM group at the 5' end

<400> SEQUENCE: 7
cagattttgg gcgggccaaa c                                             21

<210> SEQ ID NO 8
<211> LENGTH: 15
<212> TYPE: DNA
<213> ORGANISM: Artificial Sequence
<220> FEATURE:
<223> OTHER INFORMATION: Protein-Nucleic Acid (PNA) probe designed for
      the detection of L858R mutation at the exon 21 of the EGFR gene

<400> SEQUENCE: 8
agtttggcca gccca                                                    15

<210> SEQ ID NO 9
<211> LENGTH: 15
<212> TYPE: DNA
<213> ORGANISM: Artificial Sequence
<220> FEATURE:
<223> OTHER INFORMATION: Forward primer designed for detection of the
      T790M mutation in exon 21 of the EGFR gene

<400> SEQUENCE: 9
aggcagccga agggc                                                    15

<210> SEQ ID NO 10
<211> LENGTH: 18
<212> TYPE: DNA
<213> ORGANISM: Artificial Sequence
<220> FEATURE:
<223> OTHER INFORMATION: Reverse primer designed for detection of the -continued T790M mutation in exon 21 of the EGFR gene

<400> SEQUENCE: 10
cctcacctcc accgtgca                                                                              18

<210> SEQ ID NO 11
<211> LENGTH: 15
<212> TYPE: DNA
<213> ORGANISM: Artificial Sequence
<220> FEATURE:
<223> OTHER INFORMATION: Probe designed for the detection of wild-type
      EGFR gene allele in the region of the T790M mutation; the primer
      is modified with a VIC group at the 5' end

<400> SEQUENCE: 11
tgagctgcgt gatga                                                                                 15

<210> SEQ ID NO 12
<211> LENGTH: 15
<212> TYPE: DNA
<213> ORGANISM: Artificial Sequence
<220> FEATURE:
<223> OTHER INFORMATION: Probe designed for the detection of T790M
      mutant in the EGFR gene allele; the primer is modified with a
      6-FAM group at the 5' end

<400> SEQUENCE: 12
tgagctgcat gatga                                                                                 15

<210> SEQ ID NO 13
<211> LENGTH: 14
<212> TYPE: DNA
<213> ORGANISM: Artificial Sequence
<220> FEATURE:
<223> OTHER INFORMATION: Protein-Nucleic Acid (PNA) probe designed for
      the detection of T790M mutation at the exon 21 of the EGFR gene

<400> SEQUENCE: 13
tcatcacgca gctc                                                                                  14

The invention claimed is:

1. A method for the detection of mutations at the EGFR gene in a serum or plasma sample from a subject, said method comprising:
   (i) obtaining DNA from said sample;
   (ii) amplifying a nucleic acid sequence corresponding to a specific target region of the EGFR gene comprising a mutation to be detected, wherein the mutation is selected from the group consisting of the ELREA deletion in exon 19, the L858R mutation in exon 21, and the T790M mutation in exon 20, and wherein the amplifying comprises PCR using primers capable of amplifying said specific target region of the EGFR gene and a Protein-Nucleic Acid (PNA) probe capable of specifically recognizing and hybridizing with the EGFR wild-type sequence within said specific target region of the EGFR gene and thereby inhibiting the amplification of the wild-type sequence resulting in production of PCR products comprising the mutation to be detected, wherein the primers and PNA probe are selected from:
   (a) the primers of SEQ ID NOS: 1-2 and PNA probe of SEQ ID NO: 3 for amplifying the ELREA deletion; (b) the primers of SEQ ID NOS: 4-5 and PNA probe of SEQ ID NO: 8 for amplifying the L858R mutation; and (c) the primers of SEQ ID NOS: 9-10 and PNA probe of SEQ ID NO: 13 for amplifying the T790M mutation; and
   (iii) detecting PCR products obtained in (ii), wherein the detecting of the PCR products indicates that there is a mutation in the EGFR gene.

2. The method according to claim 1, wherein the detecting is carried out by means of nucleic acid sequencing.

3. The method according to claim 1, wherein the amplifying is carried out using a primer labeled with one detectable moiety and wherein the detecting is carried out by means of capillary electrophoresis.

4. The method according to claim 3, wherein the primer labeled with one detectable moiety is an oligonucleotide primer which is fluorescently labelled at its 5' end with a fluorescent dye.

5. The method of claim 4, wherein said fluorescent dye is selected from the group consisting of 6-FAM, HEX and NED dyes.

6. The method of claim 1, wherein the detecting is carried out using a 5' nuclease activity assay.

* * * * *

UNITED STATES PATENT AND TRADEMARK OFFICE
CERTIFICATE OF CORRECTION

PATENT NO. : 8,637,245 B2
APPLICATION NO. : 12/374307
DATED : January 28, 2014
INVENTOR(S) : Rafael Rosell Costa Page 1 of 1

It is certified that error appears in the above-identified patent and that said Letters Patent is hereby corrected as shown below:

On the Title page of the patent, item (73), assignee "Pangea Biotech, S.A." should be -- Pangaea Biotech, S.A. --.

Signed and Sealed this
Twenty-second Day of July, 2014

Michelle K. Lee
*Deputy Director of the United States Patent and Trademark Office*